US010968209B2

(12) United States Patent
Stoy et al.

(10) Patent No.: US 10,968,209 B2
(45) Date of Patent: Apr. 6, 2021

(54) TRPV4 ANTAGONIST

(71) Applicant: GlaxoSmithKline Intellectual Property (No.2) Limited, Brentford (GB)

(72) Inventors: Patrick Stoy, Collegeville, PA (US); Carl A. Brooks, Collegeville, PA (US); Guosen Ye, Collegeville, PA (US)

(73) Assignee: GlaxoSmithKline Intellectual Property (No.2) Limited

( * ) Notice: Subject to any disclaimer, the term of this patent is extended or adjusted under 35 U.S.C. 154(b) by 319 days.

(21) Appl. No.: 16/302,118

(22) PCT Filed: May 18, 2017

(86) PCT No.: PCT/IB2017/052936
§ 371 (c)(1),
(2) Date: Nov. 16, 2018

(87) PCT Pub. No.: WO2017/199199
PCT Pub. Date: Nov. 23, 2017

(65) Prior Publication Data
US 2020/0308160 A1 Oct. 1, 2020

Related U.S. Application Data

(60) Provisional application No. 62/338,625, filed on May 19, 2016.

(51) Int. Cl.
*C07D 413/14* (2006.01)
*A61K 9/20* (2006.01)
*A61K 9/00* (2006.01)

(52) U.S. Cl.
CPC .......... *C07D 413/14* (2013.01); *A61K 9/0019* (2013.01); *A61K 9/0053* (2013.01); *A61K 9/0073* (2013.01); *A61K 9/20* (2013.01)

(58) Field of Classification Search
CPC .. C07D 413/14; A61K 9/0019; A61K 9/0053; A61K 9/0073; A61K 9/20
USPC .................................................. 514/255.05
See application file for complete search history.

(56) References Cited

FOREIGN PATENT DOCUMENTS

| BE | 826260 | 6/1975 |
| WO | WO 12174340 | 12/2012 |
| WO | WO 12174342 | 12/2012 |
| WO | WO 2013/012500 A1 | 1/2013 |

OTHER PUBLICATIONS

Abdulqawi, et al., *The Lancet*; 385(9974):1198-1205 (2015).
Akiyama, et al., *J Investigative Dermatology*, 136: 154-160 (2016).
Alessandri-Haber, et al., *Journal of Neuroscience*, 26(14): 3864-3874 (2006).
Alvarez, et al., *Circulation Research*, 99(9): 988-995 (2006).
Auer-Grumbach, et al., *Nature Genetics*, 42(2):160-164 (2010).
Balakrishnam, et al , *Am J Physiol Lung Cell Mol Physiology*, 307: L158-72 (2014).
Basoglu, et al., *Chest.* , Aug;148(2):430-5 (2015).
Bhargave, et al.,. *Am J Rhinol*, 22:7-12 (2008).
Bonvini, et al., *J Allergy Clin Immunol*.,138(1):249-261.e12 (2016).
Chen, et al., *J Biol Chem*, 291: 10252-62 (2016).
Delany, et al., *Physiol Genomics*, 4(3):165-74 (2001).
Deng, et al, *Nature Genetics*, 42(2):165-169 (2010).
Duan, et al., *Molecular and Genetic Genomic,s* 290:1357-65 (2015).
Earley, et al., *Circ Res*, 97:1270-9 (2005).
Grant, et al., *J Physiol* 578:715-733 (2007).
Guler, et al., *J Neurosci* 22:6408-6414 (2002).
Hamanaka, et al, *Am J Physiol Lung Cell Mol Physiol*., 293(4):L923-932 (2007).
Jian, et al., *Am J Respir Cell Mol Biol*, 38:386-392 (2008).
Jie, et al., *Frontiers in Cellular Neuroscience*, 9:141 (2015).
Jo, et al., *Proc Natl Acad Sci U S A*, 113:3885-90 (2016).
Krakow, et al., *Am J Hum Genetics*, 84: 307-15 (2009).
Landoure, et al., *Nature Genetics*, 42(2):170-174 (2010).
Li, et al., *Front Cell Neuroscience*, 7:17 (2013).
Liedtke & Simon, *Am J Physiology*, 287:269-71 (2004).
Masuyama, et al., *Cell Metab* 8:257-65 (2008).
McAlexander MA, et al., *J Pharmacol Exp Ther*., 349(1):118-25 (2014).
Monaghan, et al., *PloS One*, 10: e0128359 (2015).
Morty, et al., *Am J Physiol Lung Cell Mol Physiology*, 307:L817-21 (2014).

(Continued)

*Primary Examiner* — Kristin A Vajda
(74) *Attorney, Agent, or Firm* — Hao Yin

(57) ABSTRACT

The present invention relates to a novel compound useful as a TRPV4 antagonist, specifically the compound 1-(((5S, 7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile, pharmaceutically acceptable salts thereof and pharmaceutical compositions containing the compound.
The compound of the invention can be useful in the treatment of a disease state selected from: atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, renal dysfunction, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence.

15 Claims, No Drawings

(56) References Cited

OTHER PUBLICATIONS

Muramatsu, et al., *J. Biol. Chem.*, 282:32158-67 (2007).
Powell, et al., *Bioorg Med Chem Lett*, 22:190-193 (2012).
Rahaman, et al., *J Clin Investigation*, 124:5225-38 (2014).
Rock, et al., *Nature Genetics*, 40:999-1003 (2008).
Stoy, Patrick, *Discovery and Optimization of Spirocarbamate TRPV4 Antagonists*, Medicinal Chemistry Gordon Research Conference, 1-30 (Aug. 2015).
Strotmann, et al., *Nat Cell Biol* 2: 695-702 (2000).
Thorneloe, et al., *Sci Transl Medicine*, 4:159ra148 (2012).
Todaka, et al., *J Biol Chemistry*, 279: 35133-35138 (2004).
Vergnolle, *Biochem Pharmacology*, 89:157-61 (2014).
Vriens, et al., *Proc Natl Acad Sci U S A*, 101:396-401 (2004).
Weglerski, et al., *J Biol Chemistry*, 284:2923-33 (2009).
Willette, et al., *J Pharmacol Exp Ther*, 325:466-74 (2008).
Yang, et al., *Am. J Physiology*, 290:L1267-L1276 (2006).
Ye, et al., *Cell*, 151: 96-110 (2012).
Yin, et al., *Am J Respir Cell Mol Biology*, 54:370-83 (2016).
Zhu, et al., *Hum Mol Genetics*, 18:2053-62 (2009).

TRPV4 ANTAGONIST

This application is a 371 of International Application No. PCT/IB2017/052936, filed 18 May 2017, which claims priority to U.S. Provisional Application 62/338,625, filed 19 May 2016, all of which are incorporated herein in their entireties.

FIELD OF THE INVENTION

The present invention relates to a novel compound useful as a TRPV4 antagonist, specifically the compound 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile, pharmaceutically acceptable salts thereof and pharmaceutical compositions containing the compound.

BACKGROUND OF THE INVENTION

TRPV4 is a member of the Transient Receptor Potential (TRP) superfamily of cation channels and is activated by heat, demonstrating spontaneous activity at physiological temperatures (Guler et al., 2002. *J Neurosci* 22: 6408-6414). Consistent with its polymodal activation property TRPV4 is also activated by hypotonicity and physical cell stress/pressure (Strotmann et al., 2000. *Nat Cell Biol* 2: 695-702), through a mechanism involving phospholipase A2 activation, arachidonic acid and epoxyeicosatrienoic acid generation (Vriens et al., 2004. *Proc Natl Acad Sci USA* 101:396-401). In addition, amongst other mechanisms proposed, tyrosine kinase activity, as well as protein kinase A and C, may also regulate TRPV4 (Wegierski et al., 2009. *J Biol Chem.* 284: 2923-33; Fan et al., 2009. *J Biol Chem* 284: 27884-91).

Heart failure results in the decreased ability of the left ventricle to pump blood into the peripheral circulation as indicated by a reduced ejection fraction and/or left ventricular dilation. This increases the left ventricular end diastolic pressure resulting in enhanced pulmonary blood pressures. This places the septal barrier, which separates the circulatory aqueous environment and the alveolar airspaces of the lung, at risk. Increased pulmonary pressure results in the flow of fluid from the pulmonary circulation into the alveolar space resulting in lung edema/congestion, as is observed in patients with congestive heart failure.

TRPV4 is expressed in the lung (Delany et al., 2001. *Physiol. Genomics* 4: 165-174) and its level of expression is up-regulated in individuals with congestive heart failure (Thorneloe et al., 2012. *Sci Transl Med* 4: 159ra148). TRPV4 has been shown to mediate $Ca^{2+}$ entry in isolated endothelial cells and in intact lungs (Jian et al., 2009. Am J Respir Cell Mol Biol 38: 386-92). Endothelial cells are responsible for forming the capillary vessels that mediate oxygen/carbon dioxide exchange and contribute to the septal barrier in the lung. Activation of TRPV4 channels results in contraction of endothelial cells in culture and cardiovascular collapse in vivo (Willette et al., 2008. *J Pharmacol Exp Ther* 325: 466-74), at least partially due to the enhanced filtration at the septal barrier evoking lung edema and hemorrage (Alvarez et al., 2006. *Circ Res* 99: 988-95). Indeed, filtration at the septal barrier is increased in response to increased vascular and/or airway pressures and this response is dependent on the activity of TRPV4 channels (Jian et al., 2008. *Am J Respir Cell Mol Biol* 38:386-92). Consistent with these observations, TRPV4 antagonists prevent and resolve pulmonary edema in heart failure models (Thorneloe et al., 2012). Overall this suggests a clinical benefit of inhibiting TRPV4 function in the treatment of acute and/or chronic heart failure associated lung congestion.

Additional benefit is suggested in inhibiting TRPV4 function in pulmonary-based pathologies presenting with symptoms including lung edema/congestion, infection, inflammation, pulmonary remodeling and/or altered airway reactivity. A genetic link between TRPV4 and chronic obstructive pulmonary disorder (COPD) has recently been identified (Zhu et al., 2009. *Hum Mol Genetics,* 18: 2053-62) suggesting potential efficacy for TRPV4 modulation in treatment of COPD with or without coincident emphysema. Enhanced TRPV4 activity is also a key driver in ventilator-induced lung injury (Hamanaka et al., 2007. *Am J Physiol* 293: L923-32) and it is suggested that TRPV4 activation may underlie pathologies involved in acute respiratory distress syndrome (ARDS), pulmonary fibrosis (Rahaman et al., 2014. *J Clin Invest* 124: 5225-38), cough (Bonvini et al., 2016 *J Allergy Clin Immunol* 138: 249-61) and asthma (Liedtke & Simon, 2004. *Am J Physiol* 287: 269-71). A potential clinical benefit for TRPV4 blockers in the treatment of sinusitis, as well as allergic and non-allergic rhinitis is also supported (Bhargave et al., 2008. *Am J Rhinol* 22:7-12).

TRPV4 has been shown to be involved in Acute Lung Injury (ALI). Chemical activation of TRPV4 disrupts the alvelor septal blood barrier potentially leading to pulmonary edema (Alvarez et al, *Circ Res.* 2006 Oct. 27; 99(9):988-95). In animal models, TRPV4 antagonism attenuates lung damage induced by chemical agents and biological toxins such as HCl, chlorine gas, and platelet activating factor (Balakrishna et al., 2014. *Am J Physiol Lung Cell Mol Physiol* 307: L158-72; Morty et al., 2014. *Am J Physiol Lung Cell Mol Physiol* 307: L817-21; Yin et al., 2016. *Am J Respir Cell Mol Biol* 54: 370-83). In addition, TRPV4 is necessary in a process known to cause or worsen ALI in humans (Hamanaka et al, *Am J Physiol Lung Cell Mol Physiol.* 2007 October; 293(4):L923-32). Overall this suggests a clinical benefit of inhibiting TRPV4 function in the treatment of ARDS and ALI.

Furthermore, TRPV4 has in recent years been implicated in a number of other physiological/pathophysiological processes in which TRPV4 antagonists are likely to provide significant clinical benefit. These include various aspects of pain (Todaka et al., 2004. *J Biol Chem* 279: 35133-35138; Grant et al., 2007. *J Physiol* 578: 715-733; Alessandri-Haber et al., 2006. *J Neurosci* 26: 3864-3874), genetic motor neuron disorders (Auer-Grumbach et al., 2009. *Nat Genet.* PMID: 20037588; Deng et al., 2009. *Nat Genet PMID:* 20037587; Landoure et al., 2009. *Nat Genet.* PMID: 20037586), cardiovascular disease (Earley et al., 2005. *Circ Res* 97: 1270-9; Yang et al., 2006. *Am. J Physiol.* 290: L1267-L1276), bone related disorders [including osteoarthritis (Muramatsu et al., 2007. *J. Biol. Chem.* 282: 32158-67), genetic gain-of function mutations (Krakow et al., 2009. *Am J Hum Genet* 84: 307-15; Rock et al., 2008 *Nat Genet* 40: 999-1003) and osteoclast differentiation (Masuyama et al. 2008. *Cell Metab* 8: 257-65)], itch (Akiyama et al., 2016. *J Invest Dermatol* 136: 154-60; Chen et al., 2016. *J Biol Chem* 291: 10252-62), stroke and disorders associated with cerebral edema (Li et al., 2013. *Front Cell Neurosci* 7: 17; Jie et al., 2015. *Front Cell Neurosci* 9: 141), inflammatory bowel disorders (Vergnolle, 2014. *Biochem Pharmacol* 89: 157-61), various diseases of the eye including glaucoma and retinopathy (Monaghan et al., 2015. *PloS One* 10: e0128359; Jo et al., 2016. *Proc Natl Acad Sci USA* 113: 3885-90), and metabolic syndrome including obesity and diabetes (Ye et al., 2012. *Cell* 151: 96-110; Duan et al., 2015. Mol Genet Genomics 290: 1357-65).

International Application No. PCT/US2012/042622, having an International filing date of Jun. 15, 2012; which also has International Publication Number WO 2013/012500 and an International Publication date of Jan. 24, 2013, describes a group of substituted azaspiro[4.5]decan-7-yl compounds which are indicated as having TRPV4 antagonist activity and which are indicated as being useful in the treatment of various diseases including sepsis, hypertension, inflammation, bone related dysfunctions, heart related dysfunctions, lung related dysfunctions, pain, motor neuron disorders, renal dysfunction, osteoarthritis, crohn's disease, colitis, irritable bowel syndrome (IBS), celiac disease and lactose intolerance. WO 2013/012500 does not generically or specifically disclose or claim any 7-hydroxy substituted azaspiro[4.5]decan-7-yl compounds. WO 2013/012500 does not generically cover or specifically disclose 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile.

The preference for a 7-methyl substituent on a substituted azaspiro[4.5]decan-7-yl TRPV4 antagonist was presented by: Stoy, *Discovery and Optimization of Spirocarbamate TRPV4 Antagonists*, Medicinal Chemistry Gordon Research Conference, August 2015.

SUMMARY OF THE INVENTION

This invention relates to the novel compound: 1-(((5S, 7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile (hereinafter "Compound A") and pharmaceutically acceptable salts thereof. This compound is represented by the following structure:

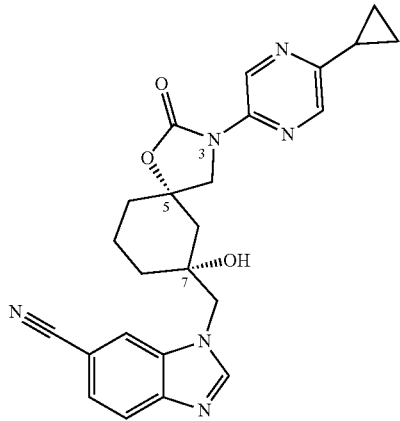 [SMILES: N#Cc1ccc2ncn(C[C@@]3(O)CCC[C@@]4(CN(c5cnc(C6CC6)cn5)C(=O)O4)C3)c2c1]

Compound A

In another aspect, this invention provides for Compound A for use in therapy.

In another aspect, this invention provides for the use of Compound A as a TRPV4 antagonist.

In another aspect, this invention provides for the use of Compound A for treating conditions associated with TRPV4 imbalance.

In another aspect, this invention provides a method of treating a disease state selected from: atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, renal dysfunction, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence, which comprises administering to a subject, suitably a human subject, in need thereof a therapeutically effective amount of Compound A.

In another aspect, this invention provides Compound A for use in the treatment of a disease state selected from: atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, renal dysfunction, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence.

In another aspect, this invention provides for the use of Compound A in the manufacture of a medicament for the treatment of a disease state selected from: atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, renal dysfunction, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence.

In another aspect, the TRPV4 antagonist may be administered alone or in conjunction with one or more other therapeutic agents, eg. agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, leukotriene antagonist, HMG-CoA reductase inhibitors, dual non-selective β-adrenoceptor and α$_1$-adrenoceptor antagonists, type-5 phosphodiesterase inhibitors, and renin inhibitors.

Other aspects and advantages of the present invention are described further in the following detailed description of the preferred embodiments.

DETAILED DESCRIPTION OF THE INVENTION

The present invention is directed to the novel compound 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile (Compound A) and pharmaceutically acceptable salts thereof, processes for its preparation, pharmaceutical formulations comprising this compound as an active ingredient, and methods for treating disease states associated with the over production of TRPV4 with Compound A or a pharmaceutically acceptable salt thereof, or a pharmaceutical formulation thereof.

WO 2013/012500 does not generically or specifically disclose or claim any 7-hydroxy substituted azaspiro[4.5]decan-7-yl compounds. WO 2013/012500 does not generically cover or specifically disclose 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of Compound A may be prepared. Indeed, in certain embodiments of the invention pharmaceutically acceptable salts of Compound A may be preferred over the respective free or unsalted compound. Accordingly, the invention is further directed to pharmaceutically acceptable salts of Compound A. The invention is further directed to the free or unsalted Compound A.

The pharmaceutically acceptable salts of the compound of the invention are readily prepared by those of skill in the art.

Compound A, and pharmaceutically acceptable salts thereof, may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water.

The skilled artisan will further appreciate that Compound A, and pharmaceutically acceptable salts thereof, may exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Biological Activity

As stated above, Compound A, and pharmaceutically acceptable salts thereof, are TRPV4 antagonists, and may be useful in the treatment disease states associated with the over production of TRPV4. Suitably, the disease state is selected from: cerebral edema, atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, motor neuron disorders, genetic gain of function disorders, cardiovascular disease, renal dysfunction and osteoarthritis.

The biological activity of Compound A can be determined using any suitable assay for determining the activity of a candidate compound as a TRPV4 antagonist, as well as tissue and in vivo models.

The biological activity of Compound A is demonstrated by the following test.

Ligand-Gated Assay:

FLIPR Assay for Human TRPV4 Expressed in HEK293 MSRII Cells

TRPV4 channel activation results in an influx of divalent and monovalent cations including calcium. The resulting changes in intracellular calcium were monitored using a calcium specific fluorescent dye Fluo-4 (MDS Analytical Technologies). HEK293 MSRII cells (human embryonic kidney 293 cells stably expressing the macrophage scavenger receptor class II) transduced with BacMam virus expressing the human TRPV4 gene at 1% final concentration were plated in a 384 well poly-D lysine coated plate (15,000 cells/well in 50 μL culture medium containing DMEM/F12 with 15 mM HEPES, 10% FBS, 1% Penicillin-Streptomycin and 1% L-glutamine). Cells were incubated for 24-72 hours at 37° C. and 5% $CO_2$. Culture medium was then aspirated using a Tecan plate-washer and replaced with 20 μL/well of dye loading buffer: HBSS, 500 μM Brilliant Black (MDS Analytical Technologies), and 2 μM Fluo-4 AM. Dye loaded plates were then incubated in the dark at room temperature for 1-1.5 hours. 10 μL of test compounds diluted in HBSS (with 1.5 mM Calcium Chloride, 1.5 mM Magnesium Chloride and 10 mM HEPES, pH 7.4)+0.01% Chaps was added to each individual well of the plate, incubated for 10 min at room temperature in the dark and then 10 μL of agonist (N—((S)-1-(((R)-1-((2-cyanophenyl)sulfonyl)-3-oxoazepan-4-yl)amino)-4-methyl-1-oxopentan-2-yl)benzo[b]thiophene-2-carboxamide, Thorneloe et al, *Sci. Transl. Med.* (2012), 4, 159ra148) (hereinafter: Agonist Compound) was added to have a final concentration equals to the agonist $EC_{80}$. Calcium signals were measured using FLIPR$^{TETRA}$ (MDS Analytical Technologies) or FLIPR384 (MDS Analytical Technologies) and the inhibition of Agonist Compound-induced calcium signal by the test compound was determined.

Compound A exhibited an activity of 6.3 nM when tested generally according to the above Ligand-gated assay.

Methods of Use

Compound A, and pharmaceutically acceptable salts thereof, may be useful as a TRPV4 antagonist and in the treatment or prevention of a disease state selected from: atherosclerosis, disorders related to vasogenic edema, post-surgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough; including acute cough, sub-acute cough and chronic cough, pulmonary hypertension, overactive bladder, cystitis, pain, motor neuron disorders, genetic gain of function disorders, cardiovascular disease, renal dysfunction, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence. Accordingly, in another aspect the invention is directed to methods of treating such conditions.

In an embodiment, this invention provides Compound A for use in the treatment of congestive heart failure.

In an embodiment, this invention provides Compound A for use in the treatment of acute lung injury.

In an embodiment, this invention provides for the use of Compound A in the manufacture of a medicament for the treatment of congestive heart failure.

In an embodiment, this invention provides for the use of Compound A in the manufacture of a medicament for the treatment of acute lung injury.

Chronic cough is highly prevalent worldwide and is highly impactful on the quality of life for suffers, with typical cough rates of 10-50 coughs per hour, during waking hours. It is hypothesized that chronic cough reflects a state of neuronal hypersensitivity involving exaggerated spinal and cortical responses to afferent sensory signals in a manner similar to chronic pain. Activation of TRPV4 channels in vivo causes ATP release and triggers afferent sensory signals from the lung through binding of ATP to P2X3 channels, resulting in cough (Bonvini, JACI, 2016). ATP levels are increased in exhaled breath of patients with diseases associated with cough, for example COPD (Basoglu, Chest, 2015).

Recently a P2X3 antagonist has demonstrated high level efficacy in reducing chronic cough and improving quality of life scores in a phase 2 clinical trial (Abdulqawi, Lancet, 2015). These clinical data along with data from pre-clinical models suggests a role for TRPV4 receptors in generating cough. TRPV4 receptors are expressed in airway smooth muscle cells (McAlexander, JPET, 2014), in airway epithelial cells (Delany, Physiol Genomics, 2001), and in sensory neurons in the lung, including Ad-fibers from airway specific afferent neurons (Bonvini, JACI, 2016). Taken together, these data suggest a potential therapeutic role for TRPV4 antagonists in cough; including acute cough, sub-acute cough and chronic cough.

Abdulqawi R, et al. *Lancet*. 2015 Mar. 28; 385(9974):1198-1205.

Basoglu O K, et al., Chest. 2015 August; 148(2):430-5.

Bonvini S J, et al., J Allergy Clin Immunol. 2016 July; 138(1):249-261.e12.

Delany N S, et al., Physiol Genomics. 2001 Jan. 19; 4(3): 165-74.

McAlexander M A, et al., J Pharmacol Exp Ther. 2014 April; 349(1):118-25.

The Compound A is tested for its ability to treat cough in in vivo in pre-clinical models in which cough is induced, for example the guinea pig model cited in Bonvini et al. above. The efficacy of Compound A is tested for its ability to treat cough; including acute cough, sub-acute cough and chronic cough in people using the objective cough monitoring and specific quality of life instruments as cited in Abdulqawi et al.

The methods of treatment of the invention comprise administering a safe and effective amount of Compound A, or a pharmaceutically acceptable salt thereof to a mammal, suitably a human, in need thereof.

As used herein, "treat", and derivatives thereof, in reference to a condition means: (1) to ameliorate the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

The term "treating" and derivatives thereof refers to therapeutic therapy. Therapeutic therapy is appropriate to alleviate symptoms or to treat at early signs of disease or its progression.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to Compound A, or a pharmaceutically acceptable salt thereof, means an amount of the compound sufficient to treat the patient's condition but low enough to avoid serious side effects (at a reasonable benefit/risk ratio) within the scope of sound medical judgment. A safe and effective amount of the compound will vary with the particular route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient", and derivatives thereof refers to a human or other mammal, suitably a human.

The subject to be treated in the methods of the invention is typically a mammal in need of such treatment, preferably a human in need of such treatment.

In a further aspect, the invention provides Compound A, or a pharmaceutically acceptable salt thereof for use in the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough, including acute cough, sub-acute cough and chronic cough, pulmonary hypertension, overactive bladder, cystitis, pain, motor neuron disorders, genetic gain of function disorders, cardiovascular disease, renal dysfunction, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence. Suitably the invention provides for a compound of Formula (I) or a pharmaceutically acceptable salt thereof for use in the treatment of congestive heart failure. Suitably the invention provides Compound A, or a pharmaceutically acceptable salt thereof for use in the treatment of acute lung injury. Suitably the invention provides Compound A, or a pharmaceutically acceptable salt thereof for use in the treatment cerebral edema. Suitably the invention provides Compound A, or a pharmaceutically acceptable salt thereof for use in treating cough; including acute cough, sub-acute cough and chronic cough, In another aspect, the invention provides for the use of Compound A, or a pharmaceutically acceptable salt thereof in the manufacture of a medicament for the treatment of atherosclerosis, disorders related to vasogenic edema, postsurgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough, including acute cough, sub-acute cough and chronic cough, pulmonary hypertension, overactive bladder, cystitis, pain, motor neuron disorders, genetic gain of function disorders, cardiovascular disease, renal dysfunction, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, or flatulence. Suitably the invention provides for the use of a compound of Formula (I) or a phramaceutically acceptable salt thereof in the manufacture of a medicament for the treatment of congestive heart failure. Suitably the invention provides for the use of Compound A, or a pharmaceutically acceptable salt thereof in the manufacture of a medicament for the treatment of acute lung injury. Suitably the invention provides for the use of Compound A, or a pharmaceutically acceptable salt thereof in the manufacture of a medicament for the treatment of cerebral edema.

Compound A, or a pharmaceutically acceptable salt thereof, may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration. Suitably the administration is oral. Suitably the administration is intravenous. Suitably the administration is by inhalation.

Compound A, or a pharmaceutically acceptable salt thereof, may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for the compound depend on the properties of the compound, such as absorption, distribution, and half-life, which can be determined by the skilled artisan. In addition, suitable dosing regimens, including the duration such regimens are administered, for the compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose. Preferred dosages are 1-500 mg once daily or twice a day per person.

Additionally, Compound A, or a pharmaceutically acceptable salt thereof, may be administered as a prodrug. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

Compound A, or a pharmaceutically acceptable salt thereof, will normally, but not necessarily, be formulated into a pharmaceutical composition prior to administration to a patient. Accordingly, in another aspect the invention is directed to pharmaceutical compositions comprising Compound A and one or more pharmaceutically acceptable excipients.

The pharmaceutical compositions of the invention may be prepared and packaged in bulk form wherein a safe and effective amount of Compound A can be extracted and then given to the patient such as with powders or syrups. Alternatively, the pharmaceutical compositions of the invention may be prepared and packaged in unit dosage form wherein each physically discrete unit contains a safe and effective amount of Compound A. When prepared in unit dosage form, the pharmaceutical compositions of the invention typically contain from 1 mg to 1000 mg of Compound A. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

Compound A and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of Compound A once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of Compound A and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesuim stearate, calcium stearate, and talc.

Included in the present invention is a process for preparing a pharmaceutical composition containing a pharmaceutically acceptable carrier and Compound A which process comprises bringing Compound A into association with a pharmaceutically acceptable carrier.

Compound A, or a pharmaceutically acceptable salt thereof, may be administered alone or in conjunction with one or more other therapeutic agents, said agents being selected from the group consisting of endothelin receptor antagonists, angiotensin converting enzyme (ACE) inhibitors, angiotension II receptor antagonists, vasopeptidase inhibitors, vasopressin receptor modulators, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, leukotriene antagonists, HMG-CoA reductase inhibitors, dual non-selective β-adrenoceptor and $\alpha_1$-adrenoceptor antagonists, type-5 phosphodiesterase inhibitors, and renin inhibitors.

The invention also provides a pharmaceutical composition comprising from 0.5 to 1,000 mg of Compound A, or pharmaceutically acceptable salt thereof and from 0.5 to 1,000 mg of a pharmaceutically acceptable excipient.

EXAMPLES

The following examples illustrate the invention. These examples are not intended to limit the scope of the present invention, but rather to provide guidance to the skilled artisan to prepare and use the compound, compositions, and methods of the present invention. While particular embodiments of the present invention are described, the skilled artisan will appreciate that various changes and modifications can be made without departing from the spirit and scope of the invention.

The following abbreviations and terms had the indicated meanings throughout:

| Abbreviation | Meaning |
| --- | --- |
| Å | angstrom |
| aq | Aqueous |
| Boc₂O | di-tert-butyl dicarbonate |
| brine | saturated aqueous NaCl |
| CAN | ceric ammonium nitrate |
| CDI | Carbonyldiimidazole |
| CH₂Cl₂ or DCM | methylene chloride |
| CH₃CN or MeCN | Acetonitrile |
| CH₃I or MeI | methyl iodide |
| (COCl)₂ | oxalyl chloride |
| Cs₂CO₃ | cesium carbonate |
| CuCN | copper cyanide |
| CuSO₄ | copper sulfate |
| d | Day |
| DCA | dichloroacetic acid |
| DMAP | 4-dimethylaminopyridine |
| DMF | N,N-dimethylformamide |
| DMSO | Dimethylsulfoxide |
| Equiv | Equivalents |
| Et | Ethyl |
| Et₃N or TEA | Triethylamine |
| EtOH | Ethanol |
| Et₂O | diethyl ether |
| EtOAc | ethyl acetate |
| GCMS | gas chromatography-mass spectroscopy |
| h, hr | Hour |
| HATU | (2-(7-Aza-1H-benzotriazole-1-yl)-1,1,3,3-tetramethyluronium hexafluorophosphate) |
| HBr | hydrobromic acid |
| HCl | hydrochloric acid |
| HPLC | high performance liquid chromatography |
| H₂SO₄ | sulfuric acid |
| i-PrOH or IPA | Isopropanol |
| i-Pr₂NEt or DIEA | N',N'-diisopropylethylamine |
| K₂CO₃ | potassium carbonate |
| kno₃ | potassium nitrate |
| KOtBu | potassium tert-butoxide |
| LAH | lithium aluminum hydride |
| LCMS | liquid chromatography-mass spectroscopy |
| Me | Methyl |
| MeOH or CH₃OH | Methanol |
| MgSO₄ | magnesium sulfate |
| min | Minute |
| MS | mass spectrum |
| MsCl | methanesulfonyl chloride |
| MTBE | methyl tert-butyl ether |
| µW | Microwave |
| n-BuLi | n-butyllithium |
| NaBH₄ | sodium borohydride |
| NaCl | sodium chloride |
| Na₂CO₃ | sodium carbonate |
| NaH | sodium hydride |
| NaHCO₃ | sodium bicarbonate |
| NaHMDS | sodium hexamethyldisilazane |
| NaN₃ | sodium azide |
| NaOH | sodium hydroxide |
| Na₂SO₄ | sodium sulfate |
| NCS | N-chlorosuccinimide |
| NH₃ | Ammonia |
| NH₄Cl | ammonium chloride |
| NH₄OH | ammonium hydroxide |
| NiCl₂ | Nickel (II) chloride |
| NMP | N-methyl pyrrolidone |
| Pd(PPh₃)₄ | tetrakis (triphenylphosphine) palladium |
| Ph | Phenyl |
| PPTS | pyridinium p-toluenesulfonate |
| Rh/Al₂O₃ | rhodium on aluminum oxide |
| RT, rt | room temperature |
| satd | Saturated |
| SCX | strong cation exchange |
| SEM | standard error of the mean |
| SFC | supercritical fluid chromatography |
| SPE | solid phase extraction |
| TFA | trifluoroacetic acid |
| THF | Tetrahydrofuran |
| $t_R$ | retention time |

Example 1

Preparation of: 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile (Compound A)

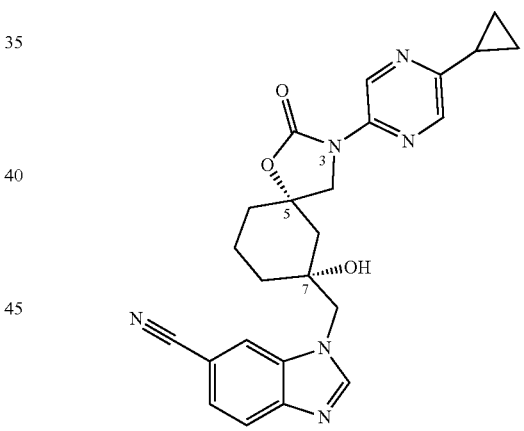

Scheme 1

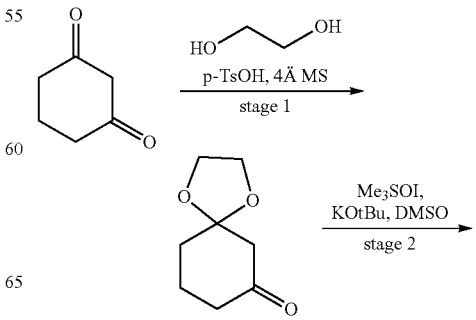

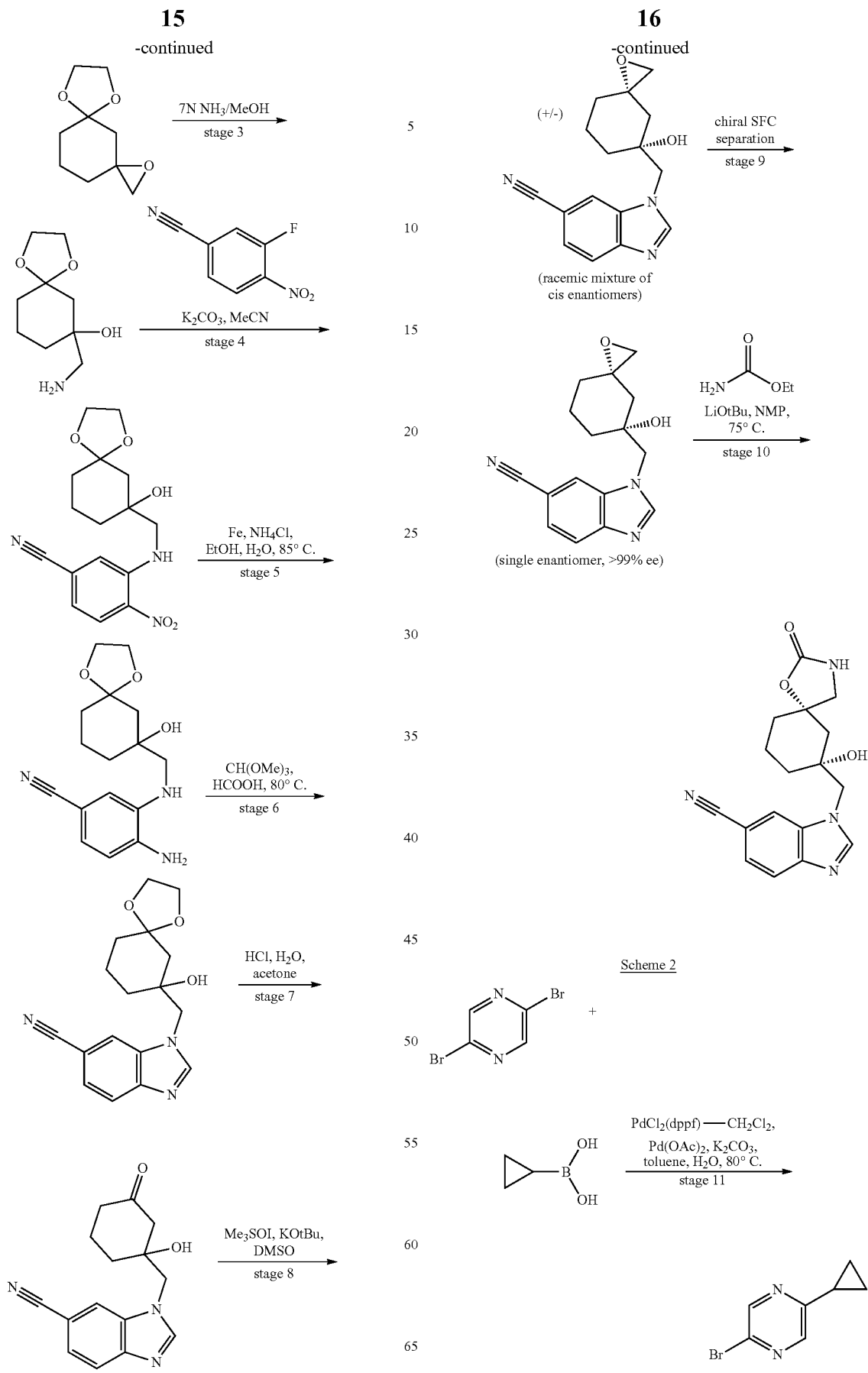

Scheme 3

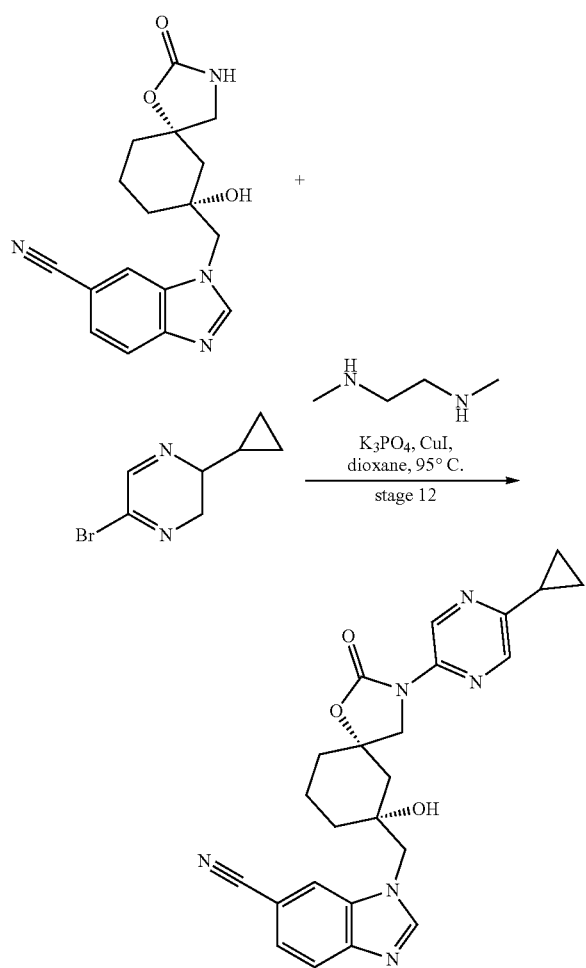

Stage 1: 1,4-dioxaspiro[4.5]decan-7-one

A solution of cyclohexane-1,3-dione (500 g, 4459 mmol), 4 Å molecular sieves (500 g, 4459 mmol), and p-toluenesulfonic acid (254 g, 1338 mmol) in dry ethylene glycol (2 L) was stirred under nitrogen at room temperature for 4 hours. The reaction mixture was diluted with saturated NaHCO$_3$ solution (1 L) to adjust to basic pH, and the basic mixture was extracted with ethyl acetate (3×1 L). The combined organic extracts were washed with brine solution (500 ml) and dried over Na$_2$SO$_4$, filtered, and concentrated under reduced pressure to afford the title compound (280 g, 1732 mmol, 38.8% yield) as a yellow liquid. LCMS (m/z) 157.1 (M+H$^+$).

Stage 2: 1,6,9-trioxadispiro[2.1.4.3]dodecane

A solution of 1,4-dioxaspiro[4.5]decan-7-one (280 g, 1793 mmol) in dimethyl sulfoxide (1.5 L) under nitrogen at 20° C. was treated with trimethylsulfoxonium iodide (395 g, 1793 mmol) and potassium tert-butoxide (221 g, 1972 mmol), and the reaction mixture was stirred for 16 hours before being diluted with water and extracted with ethyl acetate (3×2 L). The combined organic extracts were washed with brine (2×500 ml), dried over Na$_2$SO$_4$, filtered, concentrated under reduced pressure and purified by silica gel column chromatography (15% ethyl acetate/petroleum ether) to afford the title compound (170 g, 962 mmol, 53.6% yield) as a colorless oil. GCMS (m/z) 141.2, 170.2.

Stage 3: 7-(aminomethyl)-1,4-dioxaspiro[4.5]decan-7-ol

A mixture of 1,6,9-trioxadispiro[2.1.4.3]dodecane (125 g, 734 mmol) and 7 N ammonia in MeOH (2.96 L, 20.7 mol) was stirred at room temperature for 72 hours. The reaction mixture was concentrated under reduced pressure to obtain a crude solid, which was triturated with pentane and dried under vacuum to obtain the title compound (100 g, 486 mmol, 66.2% yield) as an off-white solid. GCMS (m/z) 187.2.

Stage 4: 3-(((7-hydroxy-1,4-dioxaspiro[4.5]decan-7-yl)methyl)amino)-4-nitrobenzonitrile A mixture of 7-(aminomethyl)-1,4-dioxaspiro[4.5]decan-7-ol (100 g, 534 mmol), 3-fluoro-4-nitrobenzonitrile (89 g, 534 mmol), and potassium carbonate (148 g, 1068 mmol) in acetonitrile (1 L) was stirred at room temperature under nitrogen for 18 hours. The reaction mixture was diluted with saturated NH$_4$Cl (1.5 L) and extracted with ethyl acetate (2×2 L). The combined organic extracts were washed with brine (2×200 ml), dried over Na$_2$SO$_4$, and concentrated under reduced pressure. The crude material was triturated with 2% MeOH/CH$_2$Cl$_2$ (200 ml), filtered, and washed with diethyl ether (300 ml) to afford the title compound (120 g, 356 mmol, 66.7% yield) as an orange solid. LCMS (m/z) 334.0 (M+H$^+$).

Stage 5: 4-amino-3-(((7-hydroxy-1,4-dioxaspiro[4.5]decan-7-yl)methyl)amino)benzonitrile A solution of 3-(((7-hydroxy-1,4-dioxaspiro[4.5]decan-7-yl)methyl)amino)-4-nitrobenzonitrile (120 g, 360 mmol) and ammonium chloride (193 g, 3600 mmol) in ethanol (1500 ml) and water (500 ml) under nitrogen was treated with iron (201 g, 3600 mmol). The reaction mixture was stirred at room temperature for 2 hours and then heated at 85° C. for 6 hours before being cooled to room temperature and concentrated under reduced pressure to remove ethanol. The remaining aqueous mixture was extracted with CH$_2$Cl$_2$ (2×1500 ml). The combined organic extracts were washed with saturated NaHCO$_3$ (1000 ml), brine (150 ml), dried over Na$_2$SO$_4$, filtered, and concentrated under reduced pressure to obtain the title compound (110 g, 312 mmol, 87% yield) as a pale yellow foam. LCMS (m/z) 304.0 (M+H$^+$).

Stage 6: 1-((7-hydroxy-1,4-dioxaspiro[4.5]decan-7-yl)methyl)-1H-benzo[d]imidazole-6-carbonitrile A solution of 4-amino-3-(((7-hydroxy-1,4-dioxaspiro[4.5]decan-7-yl)methyl)amino)benzonitrile (110 g, 312 mmol) and trimethyl orthoformate (34.5 ml, 312 mmol) was treated with formic acid (11.96 ml, 312 mmol) and stirred at 80° C. for 4 hours before being concentrated under reduced pressure. The residue was diluted with ethyl acetate (1.5 L) and washed with saturated NaHCO$_3$ solution (1 L), water (100 ml), and brine (100 ml). The organic layer was concentrated under reduced pressure. The material was triturated with acetone (100 ml), diethyl ether (3×300 ml), and hexane, and dried to afford the title compound (80 g, 254 mmol, 81% yield) as an off-white solid. LCMS (m/z) 314.0 (M+H$^+$).

Stage 7: 14(1-hydroxy-3-oxocyclohexyl)methyl)-1H-benzo[d]imidazole-6-carbonitrile A solution of 1-((7-hydroxy-1,4-dioxaspiro[4.5]decan-7-yl)methyl)-1H-benzo[d]imidazole-6-carbonitrile (60 g, 191 mmol) in acetone (600 ml) and water (200 ml) was treated with 1 N aqueous HCl (94 ml, 94 mmol) and stirred at room temperature for 24 hours. The reaction mixture was diluted with ethyl acetate and water, and the layers were separated. The organic layer was washed with water (500 ml). The combined aqueous extracts were washed with ethyl acetate (3×800 ml). The combined organics extracts were washed with brine, dried over $Na_2SO_4$, and concentrated under reduced pressure. The resulting material was triturated with diethyl ether (550 ml), dried, and then suspended in $CH_2Cl_2$ (500 ml) and stirred for 16 hours. The solid was collected by filtration and purified by silica gel column chromatography (0-4% MeOH/$CH_2Cl_2$) to give the title compound (30 g, 109 mmol, 57% yield) as an off-white solid. LCMS (m/z) 270.2 (M+H$^+$).

Stage 8: (+/−) 1-(((3S,5R)-5-hydroxy-1-oxaspiro[2.5]octan-5-yl)methyl)-1H-benzo[d]imidazole-6-carbonitrile (racemic mixture of cis enantiomers)

A solution of 1-((1-hydroxy-3-oxocyclohexyl)methyl)-1H-benzo[d]imidazole-6-carbonitrile (30 g, 111 mmol) and trimethylsulfoxonium iodide (27.0 g, 123 mmol) in dimethyl sulfoxide (200 ml) under nitrogen was treated with potassium tert-butoxide (13.75 g, 123 mmol) and stirred at room temperature for 1 hour. The reaction mixture was poured on to ice-water (500 ml) and extracted with ethyl acetate (6×550 ml). The combined organic extracts were washed with water (2×100 ml) and brine (100 ml), dried over $Na_2SO_4$, filtered, and concentrated under reduced pressure. The residue was triturated with 2:8 MeCN:diethyl ether (2×100 ml) and the solid was collected by filtration, rinsed with diethyl ether, and purified by silica gel column chromatography (0-3% MeOH/$CH_2Cl_2$) to give the title compound (12.5 g, 43.2 mmol, 38.8% yield) as a white solid. LCMS (m/z) 284.3 (M+H$^+$).

Stage 9: 1-(((3S,5R)-5-hydroxy-1-oxaspiro[2.5]octan-5-yl)methyl)-1H-benzo[d]imidazole-6-carbonitrile (+/−) 1-(((3S,5R)-5-hydroxy-1-oxaspiro[2.5]octan-5-yl)methyl)-1H-benzo[d]imidazole-6-carbonitrile (racemic mixture of cis enantiomers) (45 g, 159 mmol) was dissolved in 1:1 $CH_2Cl_2$: EtOH (900 ml) and the enantiomers were resolved by chiral supercritical fluid chromatography (SFC) employing a ChiralPak IC column (30×250 mm, 5 μm) under isocratic conditions (co-solvent 35% IPA, flow rate 60 gram/minute) to obtain the title compound (14.08 g, 47.22 mmol, 29.7%, >99% ee) as a pale orange solid. LCMS (m/z) 284.1 (M+H$^+$).

Stage 10: 1-(((5S,7R)-7-hydroxy-2-oxo-1-oxa-3-azaspiro[4.5]decan-7-yl)methyl)-1H-benzo[d]imidazole-6-carbonitrile A mixture of ethyl carbamate (15.47 g, 174 mmol), lithium tert-butoxide (1 M in hexanes) (17.37 ml, 17.37 mmol), and N-methyl-2-pyrrolidone (174 ml) was stirred at room temperature for 5 minutes before 1-(((3S,5R)-5-hydroxy-1-oxaspiro[2.5]octan-5-yl)methyl)-1H-benzo[d]imidazole-6-carbonitrile (9.84 g, 34.7 mmol) was added. The mixture was stirred at 75° C. for 15 hours, then cooled to room temperature, and poured into 400 ml water (warming of the mixture was observed). The resulting light orange suspension was stirred overnight and the solid was collected by filtration to afford the title compound (6.745 g, 17.57 mmol, 50.6% yield) as a pale orange solid. LCMS (m/z) 327.0 (M+H$^+$).

Stage 11: 2-bromo-5-cyclopropylpyrazine 2-bromo-5-cyclopropylpyrazine was ordered from CombiPhos Catalysts (CS2504) or synthesized using the following preparation. A solution of 2,5-dibromopyrazine (60 g, 252 mmol) in toluene (600 ml) was stirred and degassed with nitrogen for 10 minutes before a solution of $K_2CO_3$ (87 g, 631 mmol) in water (80 ml) was added. The mixture was degassed for an additional 5 minutes, then cyclopropylboronic acid (28.2 g, 328 mmol), palladium(II) acetate (2.83 g, 12.61 mmol), and $PdCl_2$(dppf)-$CH_2Cl_2$ adduct (10.30 g, 12.61 mmol) were added, and the reaction mixture was stirred at 80° C. overnight. The reaction mixture was filtered through celite, and the filtrate was diluted with ethyl acetate (400 ml) and washed with water (2×200 ml) and brine. The organic layer was dried over $Na_2SO_4$, filtered, concentrated under reduced pressure and purified by silica gel chromatography (3% ethyl acetate/hexanes) to give a yellow oil, which was dissolved in 1:9 $CH_2Cl_2$:pentane (50 ml) and cooled to −20° C. A precipitate formed and the resulting suspension was stirred for 10 minutes before the solvents were decanted and the solid was dried. The $CH_2Cl_2$:pentane process was repeated, and the solid obtained was dried under vacuum to afford the title compound (18.35 g, 88 mmol, 34.9% yield) as a white crystalline solid. GCMS (m/z) 197.0/199.0.

Stage 12: 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile A mixture of 1-(((5S,7R)-7-hydroxy-2-oxo-1-oxa-3-azaspiro[4.5]decan-7-yl)methyl)-1H-benzo[d]imidazole-6-carbonitrile (6.736 g, 20.64 mmol), 2-bromo-5-cyclopropylpyrazine (6.16 g, 31.0 mmol), and potassium phosphate, tribasic (8.76 g, 41.3 mmol) in 1,4-dioxane (138 ml) was treated with $N^1,N^2$-dimethylethane-1,2-diamine (1.819 g, 20.64 mmol) and copper(I) iodide (1.965 g, 10.32 mmol) and stirred at 95° C. for 16 hours. The mixture was then cooled to room temperature, diluted with $CH_2Cl_2$ (200 ml), water (150 ml) and 7 N $NH_3$ in MeOH (10 ml; to remove copper impurities). The layers were separated, and the aqueous layer was extracted with $CH_2Cl_2$ (2×50 ml). The combined $CH_2Cl_2$ extracts were washed with an 8:2 mixture of water and 7 N $NH_3$ in MeOH (3×50 ml), dried over $Na_2SO_4$, filtered, concentrated under reduced pressure, and purified by silica gel chromatography (0-10% methanol/dichloromethane) to give a pale orange solid. This solid was stirred in 60 ml of EtOH at 50° C. for 30 minutes, and then at room temperature overnight before being collected by filtration to afford a white solid. This solid was stirred in 40 ml of MeCN at 50° C. for 30 minutes, and then at room temperature for 1 hour and then collected by filtration to afford the title compound (3.395 g, 7.26 mmol, 35.2% yield) as a white crystalline solid. LCMS (m/z) 445.3 (M+H$^+$). $^1$H NMR (400 MHz, DMSO-$d_6$) δ ppm: 9.12 (d, J=1.5 Hz, 1H), 8.39 (s, 1H), 8.37 (d, J=1.5 Hz, 1H), 8.32 (d, J=1.2 Hz, 1H), 7.81 (d, J=8.4 Hz, 1H), 7.56 (dd, J=8.4, 1.2 Hz, 1H), 4.66 (s, 1H), 4.26 (d, J=14.6 Hz, 1H), 4.22 (d, J=14.6 Hz, 1H), 3.92

(d, J=10.2 Hz, 1H), 3.82 (d, J=10.2 Hz, 1H), 2.12-2.21 (m, 1H), 1.78-2.04 (m, 4H), 1.35-1.64 (m, 4H), 0.96-1.02 (m, 2H), 0.86-0.91 (m, 2H).

Example 2—Capsule Composition

An oral dosage form for administering the present invention is produced by filing a standard two piece hard gelatin capsule with the ingredients in the proportions shown in Table 1, below.

TABLE 1

| INGREDIENTS | AMOUNTS |
|---|---|
| 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile (Compound A) | 7 mg |
| Lactose | 53 mg |
| Talc | 16 mg |
| Magnesium Stearate | 4 mg |

Example 3—Injectable Parenteral Composition

An injectable form for administering the present invention is produced by stirring 1.7% by weight of 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile (Compound A) in 10% by volume propylene glycol in water.

Example 4—Tablet Composition

The sucrose, calcium sulfate dihydrate and Compound A as shown in Table 2 below, are mixed and granulated in the proportions shown with a 10% gelatin solution. The wet granules are screened, dried, mixed with the starch, talc and stearic acid, screened and compressed into a tablet.

TABLE 2

| INGREDIENTS | AMOUNTS |
|---|---|
| 1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile (Compound A) | 12 mg |
| calcium sulfate dihydrate | 30 mg |
| sucrose | 4 mg |
| starch | 2 mg |
| talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

The invention claimed is:

1. A compound which is:

1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile;

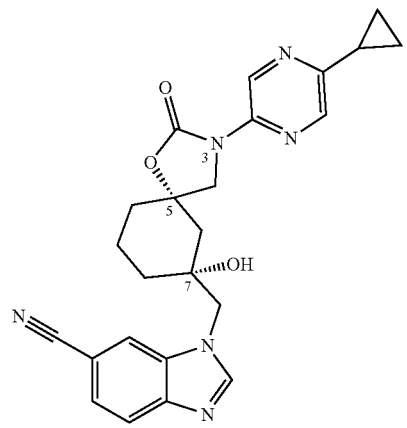 [SMILES: N#Cc1ccc2ncn(C[C@@]3(O)CCC[C@@]4(CN(c5cnc(C6CC6)cn5)C(=O)O4)C3)c2c1]

or a pharmaceutically acceptable salt thereof.

2. A compound of claim 1 which is:

1-(((5S,7R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile;

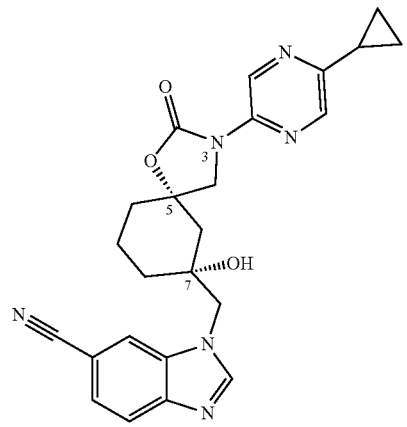

3. A compound of claim 1 which is a pharmaceutically acceptable salt of 1-(((5 S R)-3-(5-cyclopropylpyrazin-2-yl)-7-hydroxy-2-oxo-1-oxa-3-azaspiro[4.5]decan-7-yl)methyl)-1H-benzo[d]imidazole-6-carbonitrile;

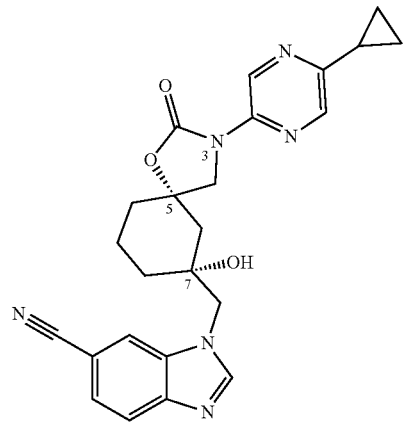

4. A pharmaceutical composition comprising a compound according to claim 1 and a pharmaceutically acceptable carrier.

5. A process for preparing a pharmaceutical composition containing a pharmaceutically acceptable carrier and a compound according to claim 1, which process comprises bringing the compound into association with a pharmaceutically acceptable carrier.

6. A method of antagonising the TRPV4 receptor in a mammal in need thereof, which comprises administering to such mammal a therapeutically effective amount of a compound according to claim 1.

7. The method of claim 6 wherein the mammal is a human.

8. A pharmaceutical composition according to claim 4, wherein the composition is in tablet form.

9. A pharmaceutical composition according to claim 4, wherein the composition is in an intravenous form.

10. A method of treating a disease state selected from: atherosclerosis, disorders related to vasogenic edema, post-surgical abdominal edema, ocular edema, cerebral edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, acute lung injury, pulmonary fibrosis, sinusitis/rhinitis, asthma, cough, acute cough, sub-acute cough, chronic cough, pulmonary hypertension, overactive bladder, cystitis, pain, motor neuron disorders, genetic gain of function disorders, cardiovascular disease, renal dysfunction, stroke, glaucoma, retinopathy, endometriosis, pre-term labor, dermatitis, pruritus, pruritus in liver disease, diabetes, metabolic disorder, obesity, migraine, pancreatitis, tumor suppression, immunosuppression, osteoarthritis, crohn's disease, colitis, diarrhea, intestinal irregularity (hyperreactivity/hyporeactivity), fecal incontinence, irritable bowel syndrome (IBS), constipation, intestinal pain and cramping, celiac disease, lactose intolerance, and flatulence, which comprises administering to a human in need thereof, a compound of claim 1.

11. A method according to claim 10 wherein the compound is administered orally.

12. A method according to claim 10 wherein the compound is administered intravenously.

13. A method according to claim 10 wherein the compound is administered by inhalation.

14. A method according to claim 10 wherein the disease is congestive heart failure.

15. A method according to claim 10 wherein the disease is acute lung injury.

* * * * *